(12) United States Patent
Fuchs

(10) Patent No.: US 6,418,475 B1
(45) Date of Patent: *Jul. 9, 2002

(54) MEDICAL IMAGING SYSTEM WITH CONTROLLED IMAGE STORAGE IN MEMORIES

(75) Inventor: Dieter Fuchs, Roettenbach (DE)

(73) Assignee: Siemens Aktiengesellschaft, Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/963,245

(22) Filed: Nov. 3, 1997

(30) Foreign Application Priority Data

Nov. 4, 1996 (DE) .......................... 196 45 419

(51) Int. Cl.⁷ .............................. G06F 15/16
(52) U.S. Cl. ...................... 709/238; 709/217
(58) Field of Search ................. 709/217, 200, 709/220, 230, 246, 250, 213, 219, 244, 238, 243; 707/1; 705/3, 2; 706/924; 345/326; 382/128; 600/300; 128/920, 922; 710/3, 4

(56) References Cited

U.S. PATENT DOCUMENTS

| | | | |
|---|---|---|---|
| 5,200,993 A | * | 4/1993 | Wheeler et al. |
| 5,280,610 A | * | 1/1994 | Travis, Jr. et al. .............. 707/1 |
| 5,384,835 A | * | 1/1995 | Wheeler et al. |
| 5,469,353 A | * | 11/1995 | Pinsky et al. .................. 705/3 |
| 5,513,101 A | * | 4/1996 | Pinsky et al. .................. 705/3 |
| 5,548,724 A | * | 8/1996 | Akizawa et al. ............. 709/203 |
| 5,559,764 A | * | 9/1996 | Chen et al. .................... 348/7 |
| 5,630,101 A | * | 5/1997 | Sieffert ....................... 709/246 |
| 5,655,084 A | * | 8/1997 | Pinsky et al. .................. 705/3 |
| 5,668,998 A | * | 9/1997 | Mason et al. ................ 706/924 |
| 5,671,353 A | * | 9/1997 | Tian et al. ..................... 705/3 |
| 5,715,823 A | * | 2/1998 | Wood et al. ................ 128/920 |
| 5,740,801 A | * | 4/1998 | Branson ..................... 128/920 |
| 5,745,681 A | * | 4/1998 | Levine et al. ............... 709/200 |
| 5,838,906 A | * | 11/1998 | Doyle et al. ................ 345/326 |
| 5,877,819 A | * | 3/1999 | Branson ..................... 348/701 |
| 5,881,311 A | * | 3/1999 | Woods .......................... 710/4 |
| 5,937,428 A | * | 8/1999 | Jantz ......................... 711/114 |
| 6,006,191 A | * | 12/1999 | DiRienzo ...................... 705/2 |

OTHER PUBLICATIONS

Newton, Harry; "Newton's Telecom Dictionary, 10th edition"; 1996; ISBN 0–936648–78–3; pp. 970–971.*

Kitney, R. et al.; Computers in Cardiology 1994; "An object oriented multi–modality display and analysis system incorporating DICOM3"; ISBN 0–8186–6570–X; pp. 181–183, Sep. 1994.*

Nicolaisen, N.; Windows Sources; "OLE & OpenDoc"; Ziff–Davis Publishing Company 1995; v3, n8, p100(6), Aug. 1995.*

Prior, F.; IEEE Proceedings of the Fourth International Confernce on Image Management and Communications, 1995, "Database access methods for medical image: DICOM, SQL and HTML"; IBSN 0–8186–7560–8; pp. 288–292, Aug. 1995.*

(List continued on next page.)

Primary Examiner—Mark H. Rinehart
Assistant Examiner—Marc D. Thompson
(74) Attorney, Agent, or Firm—Schiff Hardin & Waite

(57) ABSTRACT

A medical imaging system has a modality for acquiring images, components for processing the images, a communication linkage for the transmission of the images and memory arrangement for storing the images with a number of separate memory systems. The memory arrangement includes a control system which causes successive image datasets to be stored in separate memory systems.

7 Claims, 2 Drawing Sheets

OTHER PUBLICATIONS

Wahle, A. et al.; 18th Annual International Conference of the IEEE Engineering in Medicine and Biology Society, 1996; "DICOM–integration in a heterogeneous environment"; ISBN 0–7803–3811–1; pp. 1228–1229 vol. 3, Nov. 1996.*

"Bildgebende Systeme für die medizinische Diagnostik," Morneburg, Ed., pp. 680–697 (1995).

"Safety First. Micro Array 500s, Raid–System in 5.25" Format, Schnurer, c't, vol. 11, pp.82–83 (1992).

* cited by examiner

MEDICAL IMAGING SYSTEM WITH CONTROLLED IMAGE STORAGE IN MEMORIES

BACKGROUND OF THE INVENTION

1. Field of the Invention

The present invention is directed to a medical imaging system of the type operable in a modality for acquiring images, and having means for processing the images, means for the transmission of the images and means for storing the images including a number of separate memories.

2. Description of the Prior Art

The book "Bildgebende Systeme für die medizinische Diagnostik", edited by H. Momeburg, $3^{rd}$ Edition, 1995, pages 689 ff. discloses that image and data sequences associated with one another be respectively stored in a specific memory system in medical image systems. A problem with this generalized approach is that spontaneously occurring load peaks, that negatively influence the entire system arise within a networked system. It is also disadvantageous that all data of a given procedure are lost given outage of a memory.

Previous memory cluster solutions together with RAID technology already offer very high technical dependability and high performance, however, there are dependability gaps and performance bottlenecks at the application level in a networked environment. Imaging systems will be increasingly employed for small and mid-sized applications. Economical systems that enable system dependability, failsafe operation and high system performance with standard components are required therefor.

SUMMARY OF THE INVENTION

An object of the present invention is to provide a medical imaging system of the type initially described, which enables a good load distribution and dependable storage over the-entire imaging system.

This object is inventively achieved in an imaging system having a number of memory systems and a control system, which controls storage of the image data in the memory systems that is fashioned such that successive image datasets are stored in separate memory systems. A medical image system having self-controlled, distributed storing is thereby obtained. The distribution of the loads onto different memory systems results in peak loads being avoided. Moreover, in the case of brief-duration or longer-lasting outage of a memory system, the data can be rerouted automatically to other memory systems, so that no data jam (backlog) arises.

In an imaging system, the memory systems are-classified in memory hierarchies. On-line memories with disk storage units in RAID technology are provided for short-term storage with limited memory capacity and fast access. A memory capacity that is multiples higher, but with diminished performance, is available in a following memory level. Jukeboxes with optical disks as storage media, file servers with tape systems, etc., are usually utilized for the on-line access.

It has proven advantageous in a such an-image system when the control unit, given outage of one of the memory systems, automatically causes subsequent data to be stored in one of the other memory systems or image stores.

The control can be simplified when distributors are arranged between the memory systems and the image stores.

The control can be simplified further, and the data flow and the use of the memory systems improved, when the image datasets are additionally provided with control data. The system components are then able to control the data flow dependent on the system status autonomously and decentrally.

DESCRIPTION OF THE PREFERRED EMBODIMENTS

Figure 1:
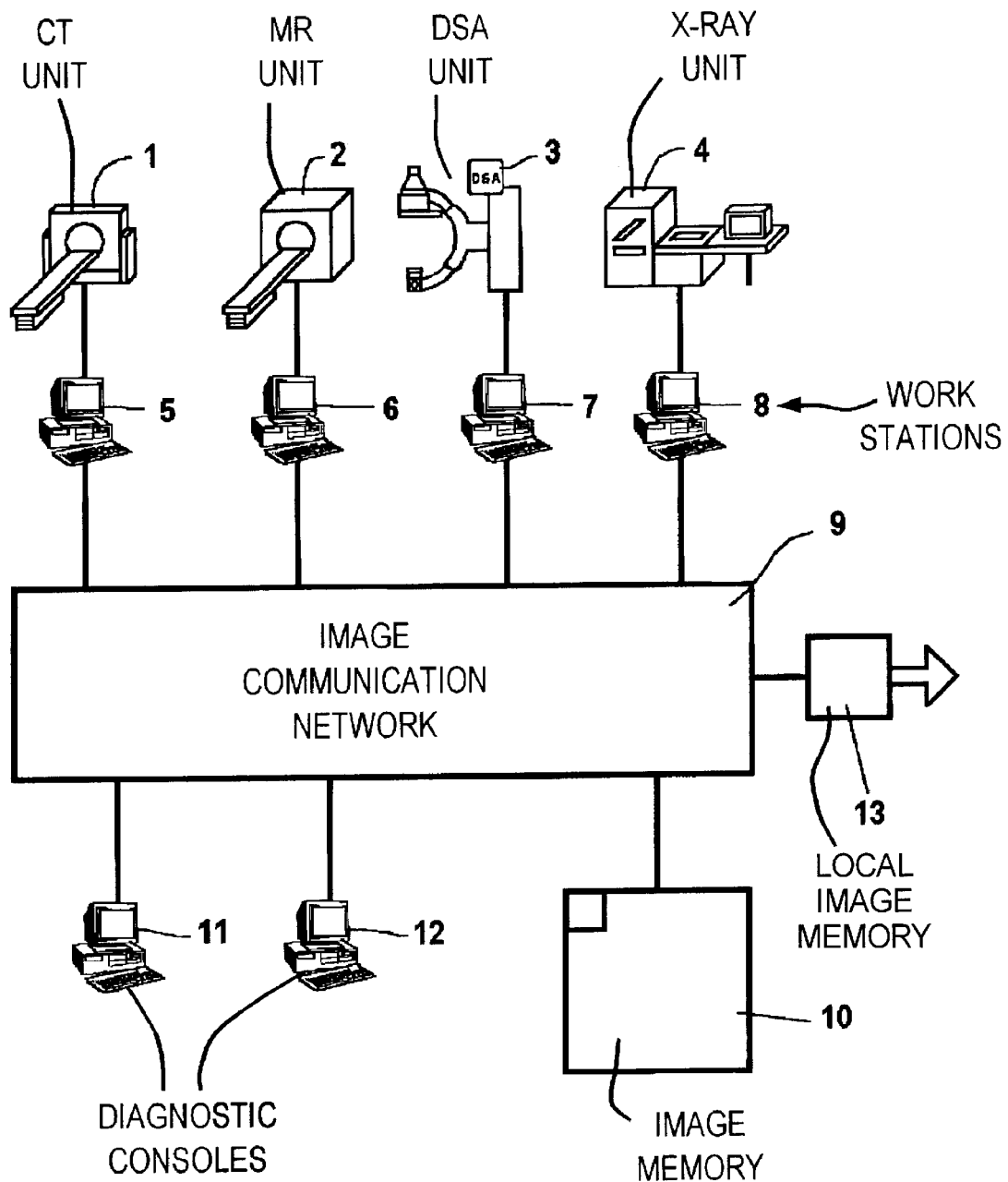
FIG. 1 shows a conventional imaging system having a networked data bank system.

FIG. 1 shows the system architecture of a conventional medical imaging communication network as an example. The modalities 1 through 4, which, for example, can include a CT unit 1 for computed tomography, an MR unit 2 for magnetic resonance imaging, a DSA unit 3 for digital subtraction angiography and an X-ray unit 4 for digital radiography as image-generating units, serve for the acquisition of medical images. Work stations 5 through 8 with which the acquired medical images can be processed and locally stored can be connected to the modalities 1 through 4. For example, such a work station can be a very fast, small computer having one or more fast processors.

The work stations 5 through 8 are connected to an image communication network 9 for the distribution of the generated images and for communication. Thus, for example, the images generated in- the modalities 1 through 4 and the images further-processed in the work stations 5 through 8 can be deposited in a central image storage system, such as an image memory 10, or can be forwarded to other work stations.

Further work stations (diagnostic consoles) 11 and 12 are connected to the image communication network 9 as diagnosis consoles that contain local image memories. The images that have been acquired and deposited in the image memory 10 can be subsequently retrieved for diagnosis in the work stations 11 and 12 and are then deposited in the work station's local image memory, from which they can be immediately available to the diagnostician working at the work station 11 or 12.

The image and data exchange via the image communication network 9 can ensue according to the DICOM standard, an industrial standard for the transmission of images and other medical information between computers for enabling digital communication between diagnostic and therapy apparatuses of different manufacturers. A network interface 13, via which the internal. image communication network 9 is connected to a global data network, can be connected to the image communication network 9, so that the standardized data can be exchanged world-wide with different networks.

Figure 2:
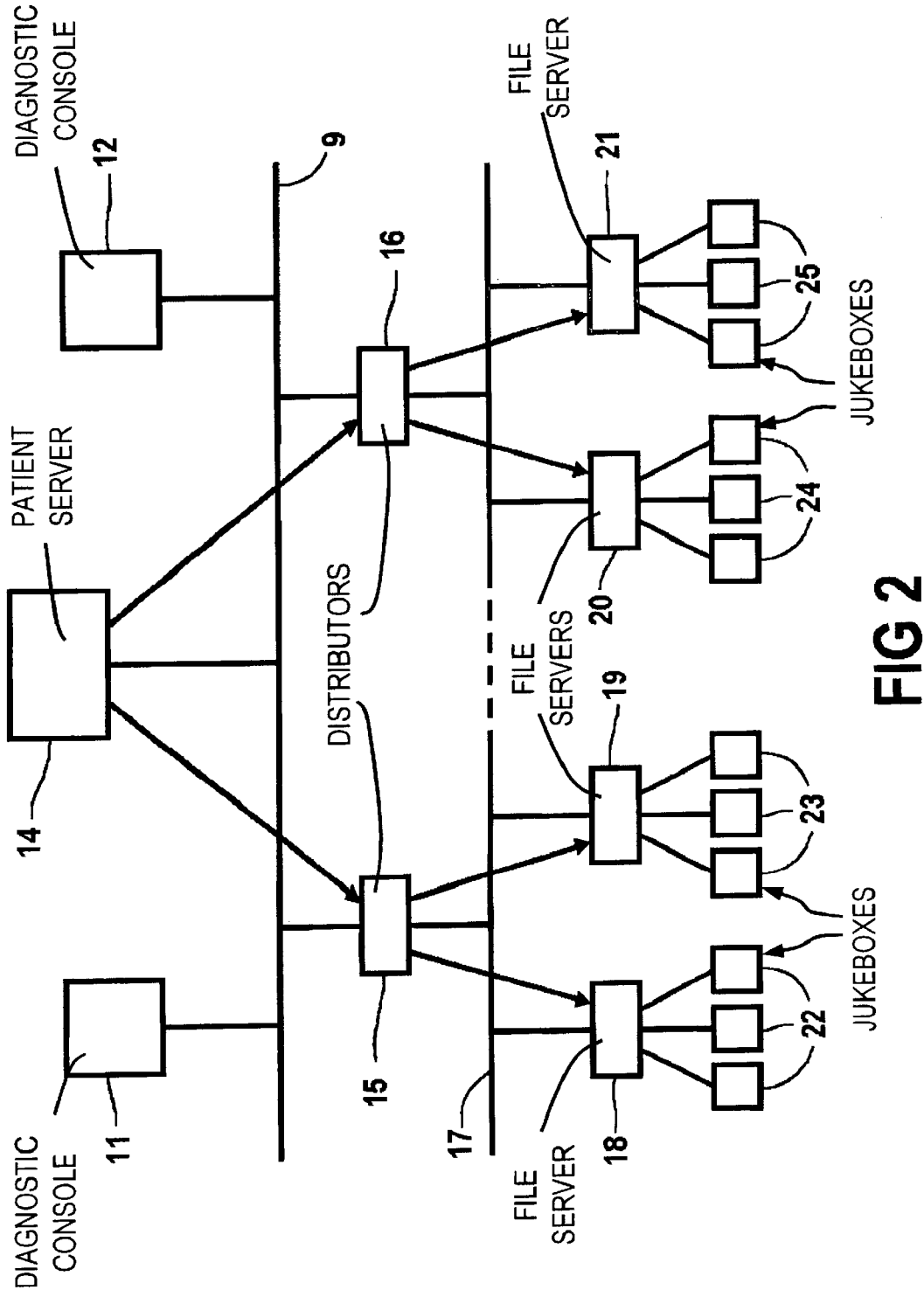
FIG. 2 shows the structure of an inventively controlled memory system for use an imaging system.

FIG. 2 shows the memory structure of an inventive imaging system in detail. In addition to the work stations 11 and 12, a patient data server 14 is connected to the image communication network 9. The patient data server 14 serves the purpose of storing the image data flow. Additionally, those memory systems and memory levels in which the appertaining image datasets are deposited are known system-wide on the basis of the patient data and control data.

File servers 18 through 21 are connected to memory systems (distributors) 15 and 16 and are also connected to a number of jukeboxes 22 through 25 serving as image memories.

The patient data server 14 and the image data communication components of the work stations 11 and 12 and distributors 15 and 16 control the storage of the image datasets such that these datasets—independently of the sender—are routed in alternation into the distributors 15 and 16 connected to the image communication network 9 and their following memory levels, for example the file servers 18 through 21, the jukeboxes 22 through 25 or other memory peripheries. Appropriately timed enablement of the various components to transmit or receive data is accomplished via control line 17. The patient data server 14 also performs the function of causing these image datasets to be relocated only via the patient data, regardless of where they are stored. A balanced load when writing as well as when reading the image data in large systems as well as in small systems is achieved as a result of this new archiving principle of distributing the data stream over a number of memory systems and memory levels.

Given outage of individual memory elements, the others automatically assume their task.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical imaging system comprising:

means for acquiring medical image data;

means for processing said medical image data;

memory means for storing said medical image data comprising a plurality of separate, individual memory systems each comprising a plurality of memory subsystems each comprising a plurality of image memories;

communication means for transferring said medical image data among said processing means and said memory systems; and control means for controlling storage of said medical image data in said memory systems for causing successive sets of said medical image data to be stored in different ones of said memory systems, said control means including a distributor for distributing said medical image data among said memory systems, and means for routing said medical image data respectively to a designated one of said plurality of image memories in one of said memory subsystems, to which said medical image data are being distributed, said means for routing including a patient data server for distributing said medical image data only via patient data.

2. A medical imaging system as claimed in claim 1 wherein each of said memory systems includes an image file system connected to said plurality of memories, and wherein said control means comprises means, given outage of one of said memory systems, for causing storage of said medical image data into a different one of said memory systems.

3. A medical imaging system as claimed in claim 2 wherein said control means comprises means, given outage of one of said image memories, for automatically causing storage of said medical image data in a different one of said image memories.

4. A medical imaging system as claimed in claim 1 wherein said image respectively comprise jukeboxes.

5. A medical imaging system as claimed in claim 1 wherein said image respectively comprise file servers.

6. A medical imaging system as claimed in claim 1 wherein said control means comprises a patient data server.

7. A medical imaging system as claimed in claim 1 wherein said means for acquiring medical image data comprises means for acquiring medical image data in a plurality of image datasets and for providing each image dataset with control data.

* * * * *